United States Patent [19]
Winkler

[11] Patent Number: 6,148,819
[45] Date of Patent: Nov. 21, 2000

[54] METHOD AND KIT FOR ADHERING A PROPHYLACTIC TO THE MALE GLANS PENIS

[75] Inventor: John Andrew Winkler, Tucson, Ariz.

[73] Assignee: John A. Winkler, Tucson, Ariz.

[21] Appl. No.: 09/396,891

[22] Filed: Sep. 15, 1999

[51] Int. Cl.[7] ................................................ A61F 6/02
[52] U.S. Cl. ........................ 128/842; 128/844; 128/918
[58] Field of Search .................................. 128/842, 844, 128/918; 604/347–353

[56] References Cited

U.S. PATENT DOCUMENTS

| | | | |
|---|---|---|---|
| 2,305,453 | 12/1942 | Martos | 128/844 |
| 3,648,700 | 3/1972 | Warner | 128/844 |
| 3,677,225 | 7/1972 | Czirely . | |
| 4,821,742 | 4/1989 | Phelps, III . | |
| 4,863,449 | 9/1989 | Therriault | 128/844 |
| 4,869,269 | 9/1989 | Sharkan . | |
| 4,869,723 | 9/1989 | Harmon | 128/844 |
| 4,888,007 | 12/1989 | Loeb | 128/844 |
| 5,069,228 | 12/1991 | Sorkin | 128/844 |
| 5,102,405 | 4/1992 | Conway . | |
| 5,421,350 | 6/1995 | Friedman . | |
| 5,458,114 | 10/1995 | Herr . | |

*Primary Examiner*—Michael A. Brown

[57] ABSTRACT

A method and a kit for adhering a glans cap, or micro-condom, to the glans of the penis. The kit contains a liquid adhesive and an applicator, a liquid solvent and an applicator, and a glans cap having a minimum of a reservoir, a pre-applied adhesive coating on the proximal surface of the annular flange, and a through-passage from the proximal surface of the annular flange into the reservoir.

20 Claims, 2 Drawing Sheets

METHOD AND KIT FOR ADHERING A PROPHYLACTIC TO THE MALE GLANS PENIS

FIELD OF THE INVENTION

Prophylactic devices which adhere only to the glans of the male's penis have difficulty adhering to the glans with the current adhesive tape technology commercially available. Adhesive tapes with enough tack to remain securely adhered to the glans are difficult to remove without causing user discomfort and duress. The instant method discloses a technique to adhere a glans cap to the male glans which affords reliability during coitus and ease of separation post coitus.

The instant method involves pre-applying a fast-curing liquid adhesive to the surface of the glans before applying a high tack tape adhesive to the glans for the purpose of securing a glans cap to the glans. The coating cured over the surface of the glans serves as a stable bonding surface for adhesion of a glans cap. A hypo-allergenic solvent is used post coitus to dissolve the coating thereby removing the glans cap from the glans penis.

BACKGROUND OF THE INVENTED METHOD

Glans caps such as U.S. Pat. Nos. 3,677,225 and 4,869,269 have been patented in the United States Patent Office for well over twenty years yet no commercially available glans cap device has been offered to the public. A significant hurdle which must be overcome is the difficulty of keeping the glans cap securely fastened to the glans during coitus. The skin of the glans is similar to skin over the remainder of the human body in that it is not a continuous, smooth surface but is instead covered with miniature crevasses. The outer most layer of skin consists of dead skin cells. When an adhesive tape is pressed to the skin of the glans the combination of dead skin cells which can be shed and crevasses over the surface both contribute to poor adhesion of the tape adhesive material. In the case of an adhesive tape securing the flange of a glans cap to the surface of the glans penis, the crevasses of the glans skin permit pre-ejaculate seminal fluid to seep between the pre-applied adhesive of the glans cap and the skin surface of the glans penis. Once seminal fluid begins to seep into the bondline area, hydro-dynamic wedging acts as a mechanism for failure of the bondline in those areas where shed skin cells haven't already caused adhesive failure.

In the instant method a curable coating is applied over the dry, clean skin of the glans penis. A cleaned skin removes skin cells about to shed. Once this coating cures it smooths over the surface of the glans by filling in the miniature crevasses of the glans epidermis and serves as a base layer to adhere the adhesive surface of a glans cap to the glans penis. The coating eliminates the risk of hydrodynamic wedging of seminal fluid between the material of the glans cap and the skin of the glans penis.

SUMMARY OF THE INVENTED METHOD

Many glans cap inventors have described concepts for pre-applying a bonding agent to the bonding surface of a glans cap. No glans cap invention previously disclosed has described a technique for preparing the glans surface for adhesion prior to bonding the glans cap in position. As with any bonding operation, proper preparation of the bonding surfaces is crucial to the performance of the bond. In the instant method a fast-curing liquid adhesive is applied to the surface of the glans penis to properly prepare it as a surface suitable for adhering the bonding agent found pre-applied to a glans cap flange. Liquid adhesives have been used in the medical industry for the purpose of securing dressings to burn victims and catheter devices to the glans penis but never for the purpose of securing a glans cap to a glans penis for coitus.

In this method the initial step is to apply a fast curing liquid adhesive, such as tincture of benzoine, gum mastic such as Mastisol by Ferndale Laboratories, purified pine tar or any other medically-approved, mildly non-polar gum to the surface of the glans penis. After the liquid adhesive has cured on the glans surface, a glans cap with its own pre-applied high-tack adhesive such as medical double-sided transfer tape similar to 3M Medical Transfer Tape #1509, is bonded to the glans penis over the surface coated by the cured liquid adhesive. This cured liquid adhesive forms a first biological barrier over the skin of the glans and establishes a continuous surface smoother than the skin of the glans as a base layer for the successful adhesion of a medical tape adhesive. A second biological barrier is formed between the cured liquid adhesive and the pre-applied adhesive tape bonding agent of the glans cap when the bonding surface of the glans cap is positioned and firmly pressed against the coated glans surface. Post coitus, the glans cap can be separated from the glans by dissolving the cured liquid adhesive with a medically-approved alcohol based solvent such as isopropyl alcohol, denatured alcohol, medically-approved petroleum distillates such as the product Detachol by Ferndale Laboratories, or soapy water or a combination thereof.

DESCRIPTION OF THE PREFERRED EMBODIMENT OF THE INVENTION

Figure 1:
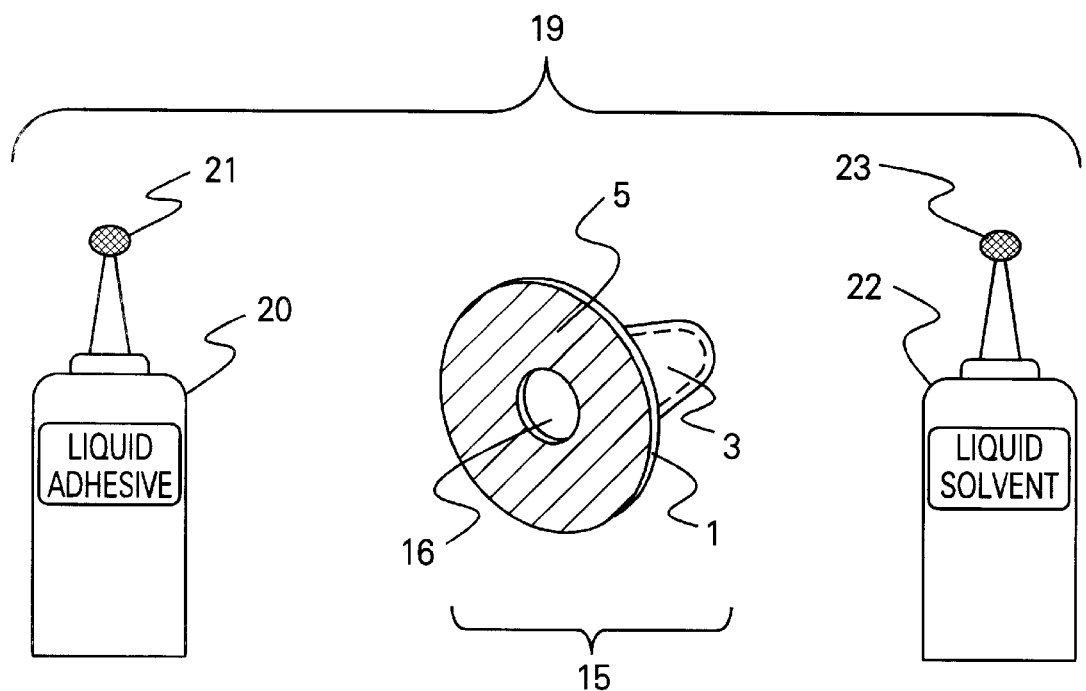
FIG. 1 shows a kit of the preferred embodiment of the invention consisting of a container of liquid adhesive with an applicator, a glans cap having a reservoir containment means and mounting flange coated with pre-applied adhesive, and a container of liquid solvent with an applicator.

The preferred embodiment of the invention consists of a kit 1 having a container 2 of liquid adhesive with an applicator 3, a glans cap 10 having a reservoir containment means 7, an orifice through passage 6 and flexible mounting flange 5 coated with pre-applied adhesive 4, and a container 8 of liquid solvent with an applicator 9. The glans cap assembly is manufactured such that a biological barrier exists between the pre-applied adhesive 4 and the surface of the mounting flange 5 of the glans cap 10.

Figure 2:
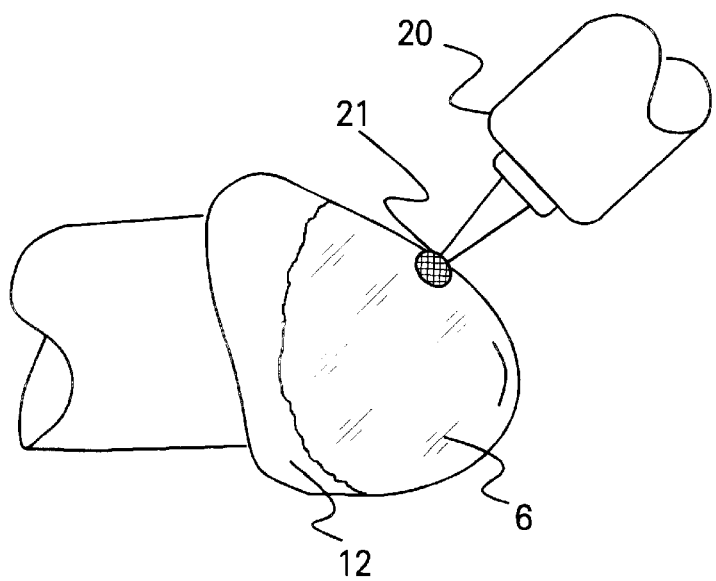
In FIG. 2, the initial step of applying a fast-curing liquid adhesive to the clean, dry surface of the glans is demonstrated.

The initial step of the instant method is shown in FIG. 2. A fast-curing liquid adhesive coating 11, such as tincture of benzoine, gum mastic such as Mastisol by Ferndale Laboratories, purified pine tar or any other medically-approved, mildly non-polar gum or a combination thereof, is applied to the skin of the glans penis 12 by means of an applicator 3 and is allowed to cure. Once cured, the coating 11 forms a first biological barrier over the skin of the glans 12.

Figure 3:
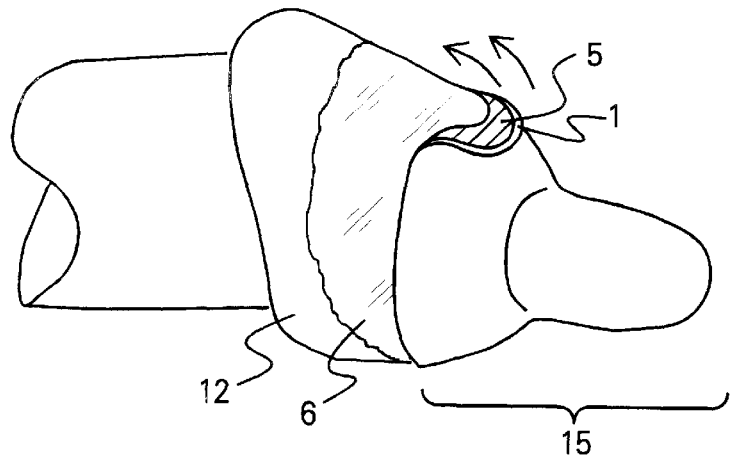
In FIG. 3, a glans cap is being bonded to the cured liquid adhesive coating the glans surface.

As shown in FIG. 3, after the liquid adhesive coating 11 has cured on the glans 12, the pre-applied adhesive 4, such as medical double-sided transfer tape similar to 3M Medical Transfer Tape #1509, covering the flange 5 of a glans cap 10 is brought into intimate contact with the coating 11 on the glans 12 and is pressed to conform against the glans. This pressing action bonds together the cured liquid adhesive 11 and the pre-applied adhesive 4 to establish a second biological barrier between the coating and the adhesive of the glans cap 10.

Figure 4:
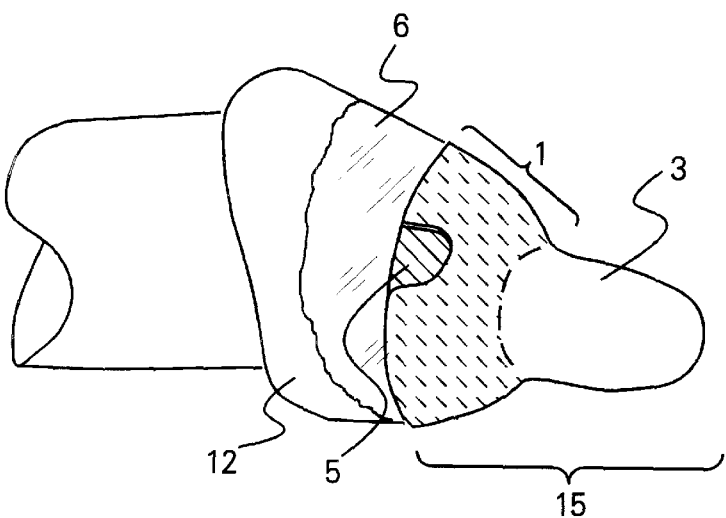
FIG. 4 shows a glans cap successfully bonded to the glans penis by the instant method.

FIG. 4 shows a glans cap 10 successfully bonded to the glans penis 12. A small portion of the flange 5 has been removed to show the pre-applied adhesive 4 of the glans cap 10 conformed to the surface of the glans 12 and bonded to the coating 11. The first biological barrier between the coating 11 and the glans penis surface 12 and the second biological barrier between the coating 11 and the glans cap adhesive 4 prevent the exchange between sexual partners of micro-organisms which can transmit venereal diseases.

Figure 5:
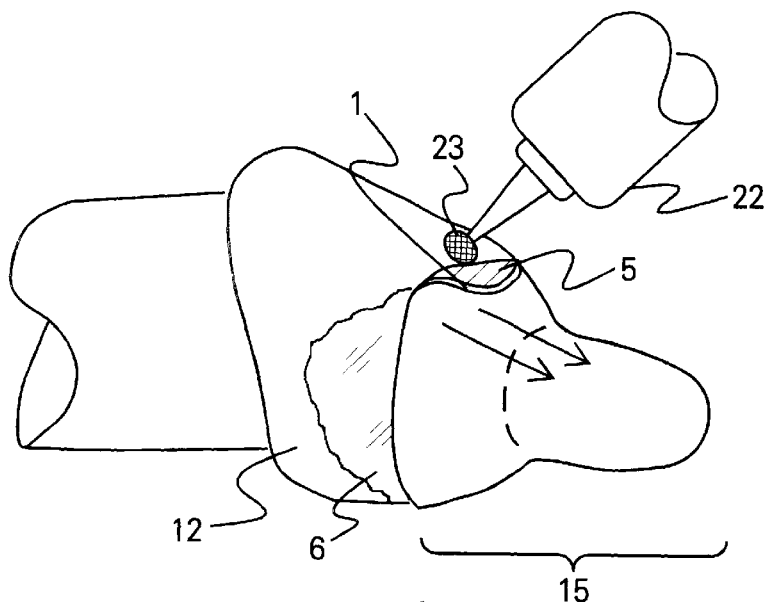
FIG. 5 shows a glans cap being removed from a glans penis post coitus by using the liquid solvent to dissolve the cured liquid adhesive.

FIG. 5 shows the glans cap 1 0 being removed from the glans penis 12 post coitus. To remove the cap 10 a solvent 8 such as isopropyl alcohol, denatured alcohol, medically-approved petroleum distillates such as the product Detachol by Ferndale Laboratories, or soapy water or a combination thereof is applied by means of an applicator 9 about the surface of the flange 5 of the glans cap 10 to dissolve the liquid adhesive coating 11 from the glans surface 12. The glans cap containing captured ejaculate is discarded after removal.

The advantage of this kit and method is that the ease of application and minimal surface area deprived of frictional stimulation reduce user apprehension towards prophylactic devices and encourage useage of a device which helps prevent unwanted pregnancies and protects the public against the transmission of venereal diseases.

While the embodiments described herein are at present considered to be preferred, it is understood that various modifications and improvements may be made therein without departing from the invention. The scope of the invention is indicated in the appended claims and all changes that come within the meaning and range of equivalency of the claims intended to be embraced therein.

I claim:

1. A method of securing a prophylactic device to the glans of a penis, wherein the prophylactic device includes a flexible flange conforming to said glans and a layer of first adhesive preapplied to the flange, comprising the following steps:
    (a) providing a liquid, second adhesive capable of bonding with the glans and with the layer of first adhesive pre-applied to the flange;
    (b) coating the glans with said second adhesive to form a continuous coat over the glans; and
    (c) after the continuous coat has dried, securing the first layer of adhesive to the coat such as to affix the prophylactic device to the glans.

2. The method of claim 1, wherein said first adhesive is transfer tape.

3. The method of claim 1, wherein said second adhesive is selected from the group consisting of tincture of benzoine, gum mastic, liquified pine tar, a non-polar gum, or mixtures thereof.

4. The method of claim 1, wherein said first adhesive is transfer tape and said second adhesive is selected from the group consisting of tincture of benzoine, gum mastic, liquified pine tar, a non-polar gum, or mixtures thereof.

5. The method of claim 1, further including the step of releasing said prophylactic device from the glans by application of a release agent.

6. The method of claim 5, wherein said release agent is an alcohol-based solvent or a petroleum distillate.

7. The method of claim 4, further including the step of releasing said prophylactic device from the glans by application of a release agent.

8. The method of claim 7, wherein said release agent is an alcohol-based solvent or a petroleum distillate.

9. A kit for securing a prophylactic device to the glans of a penis comprising:
    (a) a prophylactic device including a flexible flange conforming to said glans and a layer of first adhesive pre-applied to the flange;
    (b) a liquid, second adhesive capable of bonding with the glans and with the layer of first adhesive pre-applied to the flange; and
    (c) an applicator for coating the glans with said second adhesive to form a continuous coat over the glans.

10. The kit of claim 9, further including a release agent for releasing said prophylactic device from the glans.

11. The kit of claim 10, wherein said release agent is an alcohol-based solvent or petroleum distillate.

12. The kit of claim 9, wherein said second adhesive is selected from the group consisting of tincture of benzoine, gum mastic, liquified pine tar, a non-polar gum, or mixtures thereof.

13. A prophylactic kit for the glans of a penis comprising:
    (a) a prophylactic device including a flexible flange conforming to said glans and a layer of first adhesive pre-applied to the flange;
    (b) a liquid, second adhesive capable of bonding with the glans and with the layer of first adhesive pre-applied to the flange; and
    (c) an applicator for coating the glans with said second adhesive to form a continuous coat over the glans.

14. The kit of claim 13, wherein said first adhesive is transfer tape.

15. The kit of claim 13, wherein said second adhesive is selected from the group consisting of tincture of benzoine, gum mastic, liquified pine tar, a non-polar gum, or mixtures thereof.

16. The kit of claim 13, wherein said first adhesive is transfer tape and said second adhesive is selected from the group consisting of tincture of benzoine, gum mastic, liquified pine tar, a nonpolar gum, or mixtures thereof.

17. The kit of claim 13, further including a release agent for releasing said prophylactic device from the glans.

18. The kit of claim 17, wherein said release agent is an alcohol-based solvent or a petroleum distillate.

19. The kit of claim 17, wherein said second adhesive is selected from the group consisting of tincture of benzoine, gum mastic, liquified pine tar, a non-polar gum, or mixtures thereof.

20. The kit of claim 19, wherein said release agent is an alcohol-based solvent or a petroleum distillate.

* * * * *